United States Patent
Li et al.

(10) Patent No.: US 8,841,008 B2
(45) Date of Patent: Sep. 23, 2014

(54) LUBRICANT FOR HEAT ASSISTED MAGNETIC RECORDING

(75) Inventors: Lei Li, Wexford, PA (US); Michael Joseph Stirniman, Fremont, CA (US); Jiping Yang, San Jose, CA (US)

(73) Assignee: Seagate Technology LLC, Cupertino, CA (US)

( * ) Notice: Subject to any disclaimer, the term of this patent is extended or adjusted under 35 U.S.C. 154(b) by 261 days.

(21) Appl. No.: 13/037,226

(22) Filed: Feb. 28, 2011

(65) Prior Publication Data

US 2012/0219826 A1    Aug. 30, 2012

(51) Int. Cl.
G11B 5/66 (2006.01)
G11B 5/725 (2006.01)
C07C 43/178 (2006.01)
C07F 9/6593 (2006.01)

(52) U.S. Cl.
CPC ............ *G11B 5/725* (2013.01); *C07C 43/1786* (2013.01); *C07F 9/65815* (2013.01)
USPC ........ 428/835.8; 508/422; 508/582; 568/611; 549/455; 549/220; 558/80

(58) Field of Classification Search
USPC ............................ 508/579, 582; 549/445, 220
See application file for complete search history.

(56) References Cited

U.S. PATENT DOCUMENTS 6,608,009 B2 * 8/2003 Akada et al. .................. 508/422
6,730,403 B1 * 5/2004 Shirai et al. ................ 428/833.5

2008/0274920 A1 * 11/2008 Negoro et al. ................ 508/258
2009/0274920 A1 * 11/2009 Li et al. ........................ 428/481
2009/0291325 A1 * 11/2009 Xu et al. ....................... 428/800
2012/0251843 A1 * 10/2012 Yan et al. ..................... 428/800

FOREIGN PATENT DOCUMENTS

| WO | WO2009/066784 | 5/2009 |
| WO | WO2009/122988 | 10/2009 |
| WO | WO2010/027096 | 3/2010 |

OTHER PUBLICATIONS

Mori et al., "Effects of end groups on the trichemical reactions of lubricants at head-disk interface," Tribology Letters, vol. 17, No. 2, Aug. 2004, pp. 317-325.*
English translation of JP 2000-260017, Shirai et al., Japan, Sep. 2000.*
English machine translation of JP 2009270093, Nov. 2009, Japan.*

* cited by examiner

*Primary Examiner* — Holly Rickman
(74) *Attorney, Agent, or Firm* — Mueting, Raasch & Gebhardt P.A.

(57) ABSTRACT

Compositions for use in lubricating thin film storage media are provided, as well as storage media formed using the compositions, the compositions including one or more central cores having a cyclic group, and a plurality of arms extending from the central cores, wherein each arm comprises phenol or piperonyl. Methods of preparing the compositions are also provided. Methods of preparing storage media that incorporate the compositions therein are further provided.

15 Claims, 5 Drawing Sheets

LUBRICANT FOR HEAT ASSISTED MAGNETIC RECORDING

BACKGROUND

1. Field

The disclosure relates to compositions for use in lubricating storage media. More particularly, the disclosure relates to a lubricant for high temperature and low clearance applications and an apparatus incorporating such lubricants.

2. Background

With new recording technologies being developed, media lubricants must also be developed to meet the requirements of the advanced recording technologies. Currently, a liquid lubricant layer is disposed on top of a magnetic recording medium in order to reduce friction and wear caused by contact between the head and the disc. The lubricants generally used are linear perfluoropolyethers. However, because of newer recording technologies being developed, a premium is placed on media lubricants that have high thermal stability. For example, in the case of Heat Assisted Magnetic Recording (HAMR), where the disk surface is heated to a relatively high temperature by laser irradiation, the currently available media lubricants are unsuitable due to thermal material losses through evaporation or decomposition caused by the heating. To provide thermal stability, lubricants with high molecular weight have been used. However, these high molecular weight molecules generally suffer from low head stability, particularly at low clearance, because the size of the lubricant molecule increases with the molecular weight. As a result, head media spacing (HMS) must be reduced to increase areal density.

SUMMARY

In one aspect of the disclosure, a composition includes a central core having a cyclic group, and two or more arms extending from the central core, wherein the arms comprise at least one of phenol and piperonyl.

In another aspect of the disclosure, a composition includes a central core; and one or more arms extending from the central core, wherein the arms comprise at least one of phenol and piperonyl.

In a further aspect of the disclosure, an apparatus includes a substrate, a magnetic layer for recording information disposed on the substrate, a protective overcoat for protecting said magnetic layer, and a lubricant comprising a compound having a composition comprising a central core, and two or more arms extending from the central core, wherein the arms comprise at least one of phenol and piperonyl.

BRIEF DESCRIPTION OF THE DRAWINGS

Various aspects of a lubricant are illustrated by way of example, and not by way of limitation, in the accompanying drawings, wherein.

DETAILED DESCRIPTION

Various aspects of the present compositions for lubricating storage media are described more fully hereinafter with reference to the accompanying drawings. The present composition, however, may be embodied in many different forms and should not be construed as limited to the various aspects presented throughout this disclosure. Rather, these aspects are provided so that this disclosure will be thorough and complete, and will fully convey the scope of the present composition to those skilled in the art.

Various aspects of the present compositions will be described herein with reference to drawings that are conceptual in nature. As such, variations from the conceptual illustrations are to be expected in practice. By way of example, various regions, layers, or sections of a storage medium may be illustrated or described as rectangular, but may have rounded features and/or a gradient concentration at its edges rather than a discrete change from one region to another. Thus, these regions, layers, or sections illustrated in the drawings are not intended to limit the scope of the present composition.

It will be understood that when region, layer, or section is referred to as being "on" another region, section, or layer, it can be directly on or intervening elements may also be present. It will be further understood that when a region, layer, or section is referred to as being "formed" on another region layer, or section, it can be grown, deposited, etched, attached, connected, coupled, or otherwise prepared or fabricated on the region, layer, or section or an intervening element.

As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. The term "and/or" includes any and all combinations of one or more of the associated listed items.

Various aspects of compositions for lubricating storage media and storage media incorporating the same will now be presented. However, as those skilled in the art will readily appreciate, these aspects may be extended to other compositions and apparatus. The compositions comprise a lubricant backbone having one or more functional groups provided on each end of the backbone, and one or more functional groups provided on the backbone between the ends. The functional groups cause the lubricant molecule to bond to and lie flat on the carbon overcoat.

1. Definitions

All scientific and technical terms used in this application have meanings commonly used in the art unless otherwise specified. As used in this application, the following words or phrases have the meanings specified.

As used herein "lubricant" means long chain polymers composed of repeat units of small perfluorinated aliphatic oxides such as perfluoroethylene oxide or perfluoropropylene oxide.

As used herein, "backbone" means the main chain of a lubricant composition. The backbone portion of the composition does not bind to a substrate, such as the carbon overcoat ("COC") layer. Elements of the backbone may include carbon (C), nitrogen (N), oxygen (O), or other linker elements. The lubricant compositions may include two or more backbones attached at an anchor point or a plurality of anchor points.

As used herein, "functional group" means a substituent attached to the lubricant backbone that is capable of interacting with a surface (COC) to be lubricated. Examples of functional groups that may be used in the lubricants include hydroxyl, phenyl, piperonyl, carboxylic acid, amide, 2,3-dihydroxy-1-propoxyl, acetamide, methacrylate, methyl methacrylate and glycidyl ether. Functional groups may cause the lubricant compositions to attach to a surface through polar interactions, and generally include the property of adhering to a surface. If the bonding enhancer is methacrylate, methyl methacrylate or glycidyl ether, then ultraviolet light can optionally be used to activate the bonding enhancer.

2. Compositions

Figure 1:
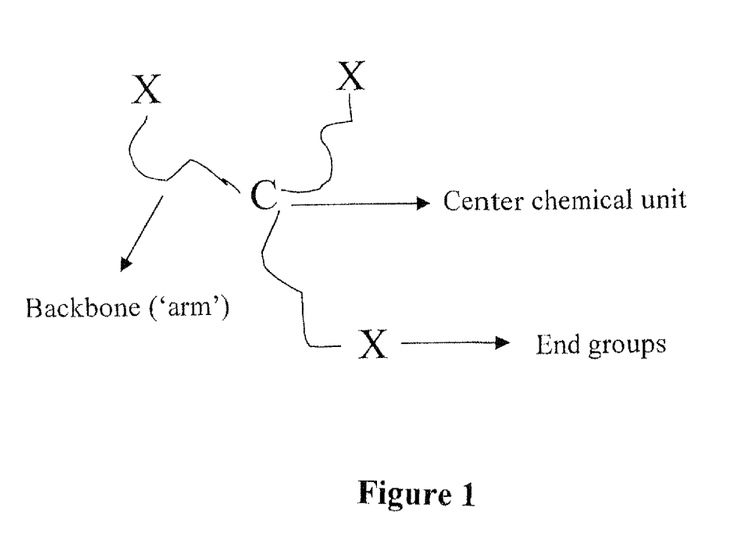
FIG. 1 is an illustration of a chemical structure of a lubricant, according to an embodiment of the current composition.

FIG. 1 is an illustration of the chemical structure of a lubricant, according to various aspects of the current composition. The chemical structure of the lubricant may include one central chemical unit, labeled "C," connected to functional end groups labeled "X" via a backbone.

Figure 2:
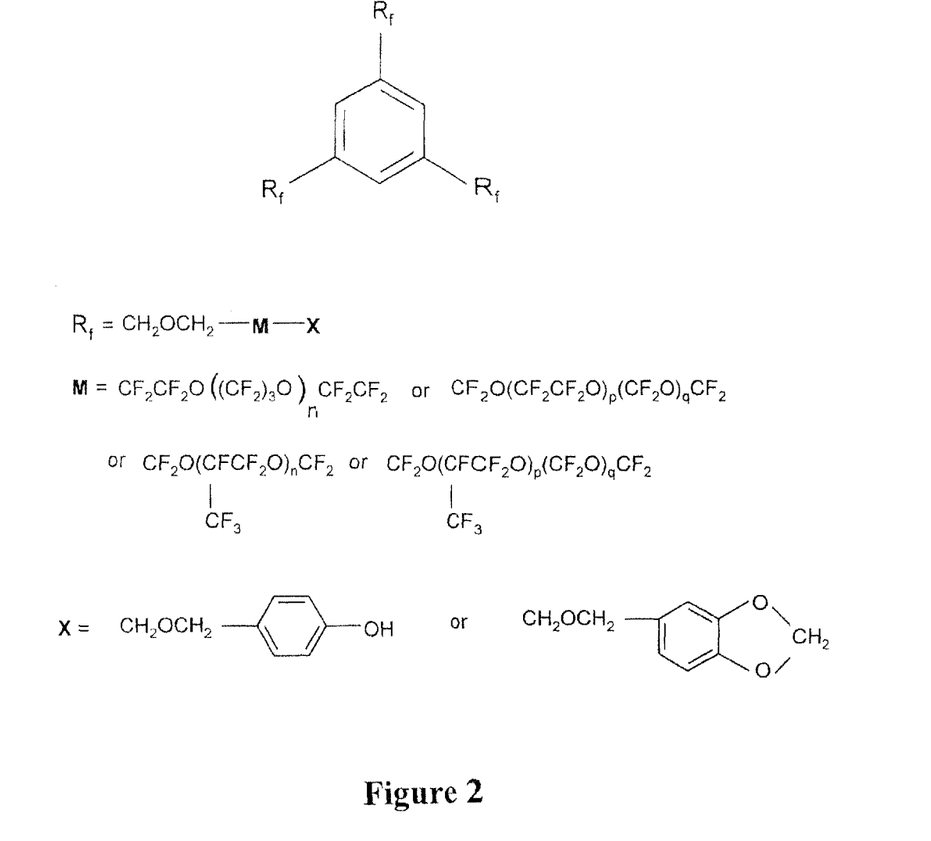
FIG. 2 is an illustration of a chemical structure of a lubricant including a central core and functional end groups, according to an embodiment of the current composition.

FIG. 2 is an illustration of the chemical structure of a lubricant including a central core and functional end groups, according to various aspects of the current composition. In FIG. 2, the central core is illustrated as a benzene ring with a three-arm structure. It should be noted that the molecule according to aspects of the current composition may have more or less than three (3) arms. As illustrated in FIG. 2, the radical end group $R_f$ may include the structure $CH_2OCH_2$-M—X, where M may include the chain $CF_2CF_2O((CF_2)_3O)_nCF_2$, $CF_2O(CF_2CF_2O)_p(CF_2O)_qCF_2$, $CF_2O(CF(CF_3)CF_2O)_nCF_2$, or $CF_2O(CF(CF_3)CF_2O)_p(CF_2O)_qCF_2$, where n, p and q are integers equal to or greater than 1. According to various aspects of the current composition, the perfluoropolyether structure of the radical group may be selected due to its high thermal stability and low surface tension. According to various aspects, the end group X may include phenol $(CH_2OCH_2C_6H_4OH)$ or piperonyl $(CH_2OCH_2C_6H_3OCH_2O)$. The aromatic structure may be selected because of its high thermal stability. For example, in order to prevent the evaporation of the lubricant, the overall molecular weight of the lubricant may be between 4000 g/mole and 20,000 g/mole. In addition, the three arms of the lubricant may be similar or different, depending on the particular application and properties of the resulting lubricant. For example, each arm may have a same or different chain structure and end groups from the other arms.

Figure 3:
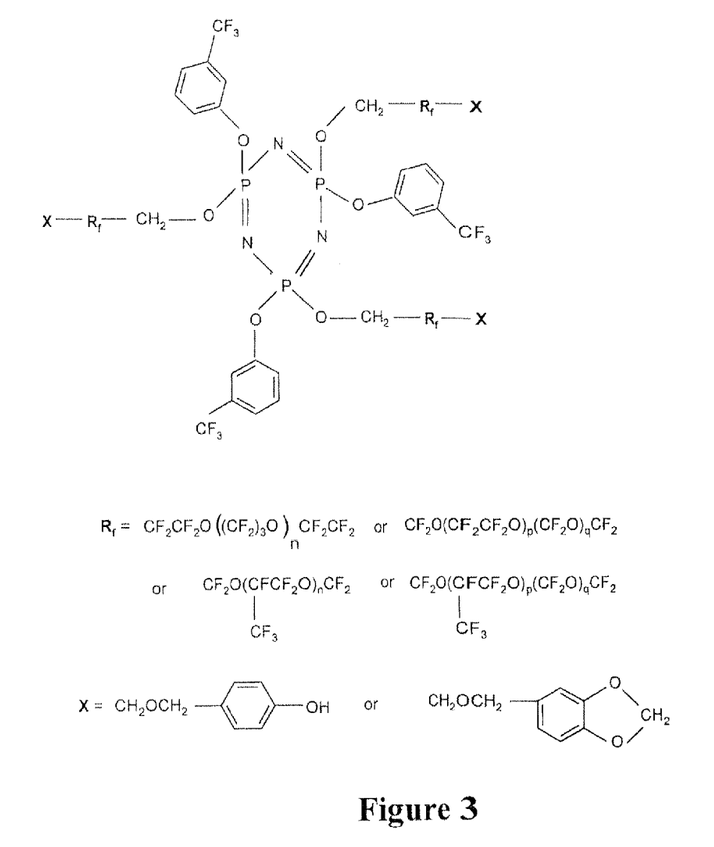
FIG. 3 is an illustration of a chemical structure of a lubricant including a central core and functional end groups, according to an embodiment of the current composition.

FIG. 3 is an illustration of the chemical structure of a lubricant including a central core and functional end groups, according to various aspects of the current composition. In FIG. 3, the chemical structure of a lubricant according to various aspects of the current composition includes a central chemical unit having a cyclotriphosphazene ring, which is a strong Lewis base and provides the thermal stability of the lubricant molecules at high temperature. The cyclotriphosphazene ring being a strong Lewis base also provides the stability of the lubricant molecules when the lubricant is in contact with Lewis acids. In the example illustrated in FIG. 3, the lubricant molecule has a three-arm structure. It should be noted that the number of arms of the lubricant may be smaller than or greater than three (3) arms. As illustrated in FIG. 3, the lubricant may include a cyclotriphosphazene ring having three (3) pairs of arms, each pair of arms including a benzene ring bonded to $CF_3(C_6H_4CF_3)$ and a functional group $OCH_2$—$R_f$—X, where the radical group $R_f$ may include the chain $CF_2CF_2O((CF_2)_3O)_nCF_2$, $CF_2O(CF_2CF_2O)_p(CF_2O)_qCF_2$, $CF_2O(CF(CF_3)CF_2O)_nCF_2$, or $CF_2O(CF(CF_3)CF_2O)_p(CF_2O)_qCF_2$, where n, p and q are integers equal to or greater than 1, and the functional group X may include phenol $(CH_2OCH_2C_6H_4OH)$ or piperonyl $(CH_2OCH_2C_6H_3OCH_2O)$. According to various aspects of the current composition, the perfluoropolyether structure may be selected due to its high thermal stability and low surface tension. The aromatic structure in a functional group of the lubricant may also be selected because of its high thermal stability. For example, in order to prevent the evaporation of the lubricant, the overall molecular weight of the lubricant may be between 4000 g/mole and 20,000 g/mole. In addition, the arms of the lubricant may be similar or different, depending on the particular application and properties of the resulting lubricant. For example, each arm may have a same or different chain structure and end groups from the other arms.

Although the examples illustrated in FIGS. 2 and 3 have structures with three arms or three pairs of arms, other star-like lubricants having similar cores and functional end groups are within the scope of this disclosure, these lubricants also may provide high temperature stability and low clearance.

Figure 4:
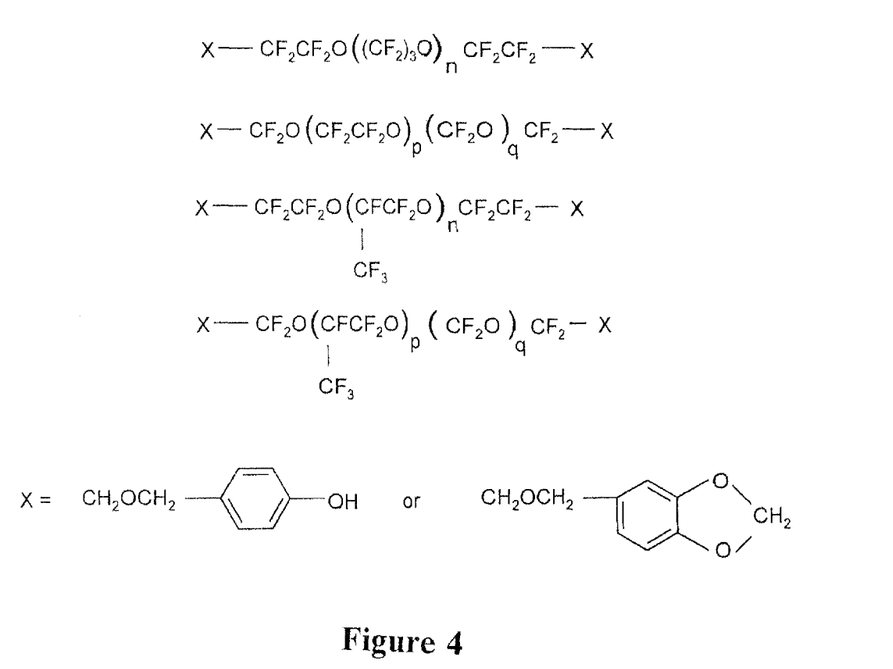
FIG. 4 is an illustration of a linear chemical structure of a lubricant including a central core and functional end groups, according to an embodiment of the current composition.

In the cases where a low clearance is not specified, then a lubricant with a linear structure may be used according to aspects of the current composition. For example, FIG. 4 is an illustration of the linear chemical structure of a lubricant including a central core and functional end groups, according to various aspects of the current composition. For example, the linear chemical structure illustrated in FIG. 4 has a backbone that may include $CF_2CF_2O(CF_2CF_2CF_2O)_nCF_2CF_2$, $CF_2O(CF_2CF_2O)_p(CF_2O)_qCF_2$, $CF_2CF_2O(CF(CF_3)CF_2O)_nCF_2CF_2$, or $CF_2O(CF(CF_3)CF_2O)_p(CF_2O)_qF_2$, where n, p and q are integers equal to or greater than 1. According to various aspects of the current composition, the end groups X attached to each arm of the backbone may be phenol $(CH_2OCH_2C_6H_4OH)$ or piperonyl $(CH_2OCH_2C_6H_3OCH_2O)$. The aromatic structure may be selected because of its high thermal stability. For example, in order to prevent the evaporation of the lubricant, the overall molecular weight of the lubricant may be between 4000 g/mole and 20,000 g/mole. In addition, the arms of the lubricant may be similar or different, depending on the particular application and properties of the resulting lubricant. For example, each arm may have a different chain structure and end groups from the other arm.

3. Methods for Lubricating, and Apparatus Incorporating the Lubricant

Methods of lubricating apparatus, such as recording media, may incorporate the compositions disclosed herein. The methods generally comprise applying the compositions to the apparatus as it is being formed. The apparatus incorporating the lubricant, such as a recording medium, may include a lubricant layer formed from the above-described compositions.

The durability and reliability of recording media may be achieved via the application of the COC and the lubricant layer. As the thickness of the carbon overcoat and lubricant protective layers is continuously reduced, greater integration of the overcoat and lubricant provides a more durable protective film. The conformation of the lubricant molecules on the carbon overcoat also contributes to the head-media spacing (HMS). In addition, lubricants that extend their molecular structure across the carbon surface may be able to cover the entire overcoat surface better than those that tend to extend their molecular chains away from the carbon surface.

According to various aspects of the current composition, the lubricant layer may be applied evenly over the recording media via a conventional dip-coating method in a thin film having a thickness from about 0.5 nm to about 2 nm on the media surface. According to various aspects of the current composition, the above thickness may be achieved by controlling the concentration of the lubricant solution and/or the pullout speed. The lubricant may also be applied on the recording media surface via vapor physical deposition or electrospray technique. As will be understood by those skilled in the art, the selection of the thickness of the lubricant layer may depend on interactions between the recording media and the head assembly, such as the static friction, or "stiction," force on the slider, air shear, and the tendency of the lubricant composition to evaporate. The amount of lubricant on the data zone may also minimize wear and damage to the disk caused by occasional contacts between the magnetic head assembly and the disk.

According to various aspects of the current composition, once the lubricant is applied on the recording media surface, thermal or other treatments such as electron beams, ultraviolet (UV) and infra-red (IR) radiation may be performed to further optimize the performance of the lubricant.

Apparatus incorporating the recording media are adapted to magnetically record information via an air bearing read/write head. The apparatus may be a computer disk drive. Those skilled in the art will appreciate that the lubricant composition and methods of preparing recording media using the lubricant composition can be incorporated into methods for manufacturing disks and disk drives, such as thin film magnetic disks and disk drives. In accordance with these methods, more durable, higher-density recording media may be provided.

Figure 5:
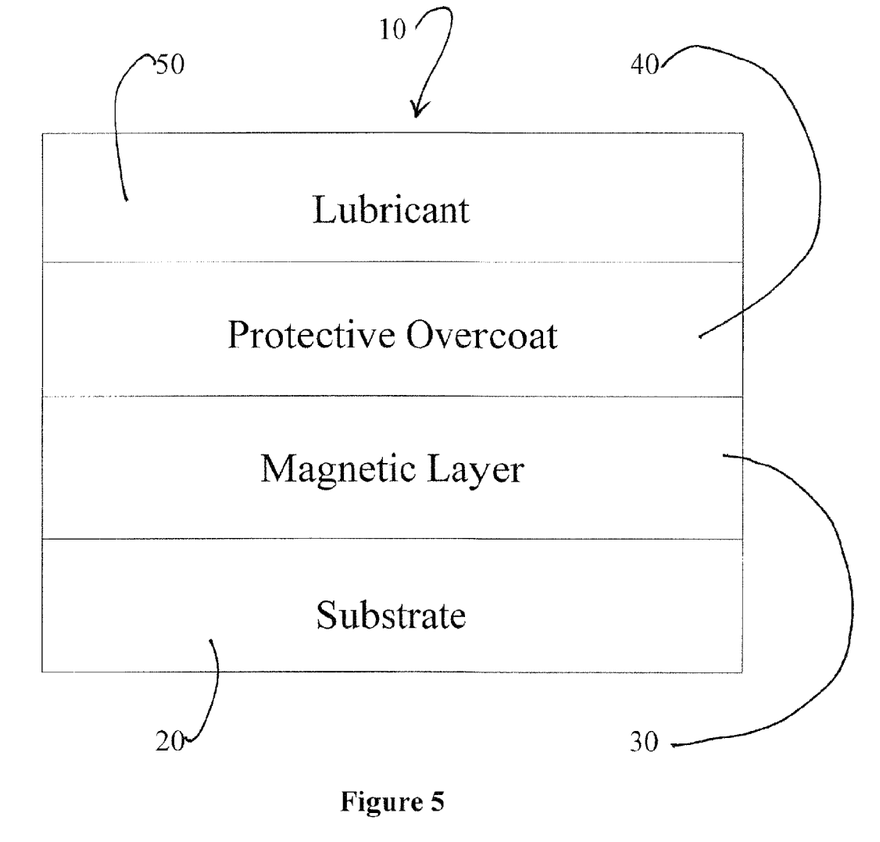
FIG. 5 is a schematic illustration of an apparatus according to an embodiment of the invention.

FIG. 5 is a schematic illustration of an apparatus 10, according to one embodiment of the invention. The apparatus includes a substrate 20, a magnetic layer for recording information disposed on the substrate 30, a protective overcoat for protecting said magnetic layer 40, and a lubricant 50. In some embodiments, the lubricant has a thickness within a range from about 0.5 nm to about and 2 nm.

The lubricant comprises a compound having a composition that includes a central core and two or more arms extending from the central core, wherein the arms comprise at least one of phenol and piperonyl. In some embodiments, the central core comprises a cyclic group. Suitable cyclic groups may be selected from the group consisting of benzene, a cyclotriphosphazene ring and derivatives thereof.

And in some embodiments each arm has the structure $CH_2OCH_2$—M—X, where M comprises one of $CF_2CF_2O((CF_2)_3O)_nCF_2$, $CF_2O(CF_2CF_2O)_p(CF_2O)_qCF_2$, $CF_2O(CF(CF_3)CF_2O)_nCF_2$, and $CF_2O(CF(CF_3)CF_2O)_p(CF_2O)_qCF_2$, where n, p and q are integers equal to or greater than 1; and where X comprises one of phenol and piperonyl. In some embodiments, the compound comprises one or more pairs of arms, such as three pairs of arms. Each pair of arms is attached to the central core. One of the pair of arms includes $C_6H_4CF_3$. The other arm of the pair of arms includes $OCH_2$—$R_f$—X; where $R_f$ includes one of $CF_2CF_2O((CF_2)_3O)_nCF_2$, $CF_2O(CF_2CF_2O)_p(CF_2O)_qCF_2$, $CF_2O(CF(CF_3)CF_2O)_nCF_2$, and $CF_2O(CF(CF_3)CF_2O)_p(CF_2O)_qCF_2$, where n, p and q are integers equal to or greater than 1; and where X includes one of phenol and piperonyl. And in some such embodiments, the central core comprises a cyclotriphosphazene ring.

The various aspects presented throughout this disclosure are provided to enable one of ordinary skill in the art to make and use the present composition. Various changes, alterations, modifications to the compounds and apparatus presented throughout this disclosure will be readily apparent to those skilled in the art, and the concepts disclosed herein may be extended to other compounds and apparatus. Thus, the claims are not intended to be limited to the various aspects of this disclosure, but are to be accorded the full scope consistent with the language of the claims. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

What is claimed is:

1. A composition comprising:
a compound having the following formula:

wherein $R_f$=$CH_2OCH_2$-M-X, and

M=$CF_2CF_2O((CF_2)_3O)_nCF_2CF_2$, $CF_2O(CF_2CF_2O)_p(CF_2O)_qCF_2$, $CF_2O(CF(CF_3)CF_2O)_nCF_2$, or $CF_2O(CF(CF_3)CF_2O)_p(CF_2O)_qCF_2$ wherein n, p, and q are integers greater than or equal to 1; and a compound having the formula wherein

$R_f$=$CF_2CF_2O((CF_2)_3O)_nCF_2CF_2$, $CF_2O(CF_2CF_2O)_p(CF_2O)_qCF_2$, $CF_2O(C(CF_3)FCF_2O)_nCF_2$, or $CF_2O(C(CF_3)FCF_2O)_p(CF_2O)_qCF_2$ wherein n, p, and q are integers greater than or equal to 1, and or
combinations thereof.

2. An apparatus, comprising:
a substrate;
a magnetic layer for recording information disposed on the substrate;
a protective overcoat for protecting said magnetic layer; and
a lubricant comprising a compound having the following formula:

wherein

$R_f$=CH$_2$OCH$_2$-M-X, and

M=CF$_2$CF$_2$O((CF$_2$)$_3$O)$_n$CF$_2$CF$_2$, CF$_2$O(CF$_2$CF$_2$O)$_p$(CF$_2$O)$_q$CF$_2$, CF$_2$O(CF(CF$_3$)CF$_2$O)$_n$CF$_2$, or CF$_2$O(CF(CF$_3$)CF$_2$O)$_p$(CF$_2$O)$_q$CF$_2$ wherein n, p, and q are integers greater than or equal to 1; and a compound having the formula wherein $R_f$=CF$_2$CF$_2$O((CF$_2$)$_3$O)$_n$CF$_2$CF$_2$, CF$_2$O(CF$_2$CF$_2$O)$_p$(CF$_2$O)$_q$CF$_2$, CF$_2$O(C(CF$_3$)FCF$_2$O)$_n$CF$_2$, or CF$_2$O(C(CF$_3$)FCF$_2$O)$_p$(CF$_2$O)$_q$CF$_2$ wherein n, p, and q are integers greater than or equal to 1, and or
combinations thereof.

3. The apparatus of claim 2, wherein the lubricant has a thickness within a range selected from a group consisting of 0.5 nm and 2 nm.

4. The composition according to claim 1, wherein the composition comprises:

wherein

$R_f$=CH$_2$OCH$_2$-M-X, and

M=CF$_2$CF$_2$O((CF$_2$)$_3$O)$_n$CF$_2$CF$_2$, CF$_2$O(CF$_2$CF$_2$O)$_p$(CF$_2$O)$_q$CF$_2$, CF$_2$O(CF(CF$_3$)CF$_2$O)$_n$CF$_2$, or CF$_2$O(CF(CF$_3$)CF$_2$O)$_p$(CF$_2$O)$_q$CF$_2$ wherein n, p, and q are integers greater than or equal to 1; and

5. The composition according to claim 4, wherein at least one Rf is different from the other two Rf.

6. The composition according to claim 4, wherein the molecular weight of the compound is from about 4000 to 20000 g/mole.

7. The composition according to claim 1, wherein the composition comprises:

wherein wherein n, p, and q are integers greater than or equal to 1, and

8. The composition according to claim 7, wherein at least one Rf-X is different from the other two Rf-X.

9. The composition according to claim 7, wherein the molecular weight of the compound is from about 4000 to 20000 g/mole.

10. The apparatus according to claim 2, wherein the lubricant comprises:

wherein

R$_f$=CH$_2$OCH$_2$-M-X, and wherein n, p, and q are integers greater than or equal to 1; and

11. The apparatus according to claim 10, wherein at least one Rf is different from the other two Rf.

12. The apparatus according to claim 10, wherein the molecular weight of the compound is from about 4000 to 20000 g/mole.

13. The apparatus according to claim 2, wherein the composition comprises:

wherein wherein n, p, and q are integers greater than or equal to 1, and

14. The apparatus according to claim 13, wherein at least one Rf-X is different from the other two Rf-X.

15. The apparatus according to claim 13, wherein the molecular weight of the compound is from about 4000 to 20000 g/mole.

* * * * *